United States Patent [19]

Isharani et al.

[11] Patent Number: 5,700,394
[45] Date of Patent: Dec. 23, 1997

[54] METHOD FOR THE TREATMENT OF TEXTILE FIBERS

[75] Inventors: Jayanti V. Isharani, Greensboro, N.C.; Willaim M. Hung; Kai C. Su, both of Alpharetta, Ga.

[73] Assignee: Ciba Specialty Chemicals Corporation, Tarrytown, N.Y.

[21] Appl. No.: 372,636

[22] Filed: Jan. 13, 1995

Related U.S. Application Data

[63] Continuation-in-part of Ser. No. 354,975, Dec. 13, 1994, abandoned.
[51] Int. Cl.$^6$ .................................................. C09K 11/06
[52] U.S. Cl. ........................ 252/301.21; 252/301.23; 8/115.59; 8/120; 8/190; 8/507; 8/549
[58] Field of Search ................... 252/301.21, 301.23; 8/115.59, 190, 120, 507, 549

[56] References Cited

U.S. PATENT DOCUMENTS

| | | | |
|---|---|---|---|
| 3,014,908 | 12/1961 | Coleman et al. | 260/249.5 |
| 3,159,646 | 12/1964 | Millonis et al. | 260/308 |
| 3,888,821 | 6/1975 | Milford, Jr. | 260/45.8 NT |
| 5,143,729 | 9/1992 | Thompson | 424/402 |

FOREIGN PATENT DOCUMENTS 3-241069   10/1991   Japan.

OTHER PUBLICATIONS

K. Yokogawa, Chem. Abst. 116:153772 S (1992).

*Primary Examiner*—Helen Lee
*Attorney, Agent, or Firm*—Kevin T. Mansfield

[57] ABSTRACT

A method for the treatment of a textile fiber to reduce the amount of UV light passing through a fabric produced from said treated fiber comprising treating a textile fiber with 0.1 to 6.0% by weight on the fiber, of a UV absorber of the formula (1)

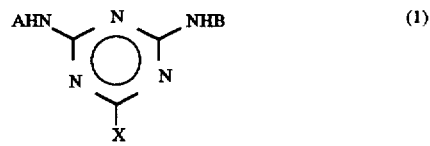

wherein A is the radical of a UV absorber, B is the radical of a UV absorber or is a water-solubilizing group and X is F or Cl, and textile fabrics and articles of clothing produced from said fabrics. Fabrics prepared from the treated fibers are useful in making clothing which provides protection against UV radiation for skin which is covered by the clothing, especially lightweight summer clothing.

16 Claims, No Drawings

METHOD FOR THE TREATMENT OF TEXTILE FIBERS

This application is a continuation-in-part of application Ser. No. 08/354,975, filed on Dec. 13, 1994, now abandoned.

The present invention relates to a method for the treatment of textile fibers, in particular to a method for the treatment of textile fibers with a UV (ultra-violet) radiation absorber containing a fiber-reactive group, and to textile fabrics produced from textile fibers so treated.

Traditionally, protection of exposed human skin against potential damage by the UV components in sunlight has been effected by directly applying to the skin a preparation containing a UV absorber. In areas of the world, e.g. Australia and the United States, which enjoy especially sunny climates, there has been a great increase in awareness of the potential hazards of undue exposure to sunlight, compounded by fears of the consequences of the alleged damage to the ozone layer. Examples of sun damage include loss of skin elasticity and the appearance of wrinkles, promotion of the onset of erythemal reaction and the inducement of phototoxic or photoallergic reactions. Some of the more extreme types of skin damage caused by excessive, unprotected exposure to sunlight are development of melanomas or carcinomas on the skin.

One aspect of the desire to increase the level of skin protection against sunlight has been the consideration of additional measures, over and above the direct protection of the skin. For example, consideration has been given to the provision of enhanced protection to skin covered by clothing and thus partially shielded from sunlight.

Most natural and synthetic textile materials are at least partially permeable to the UV portion of sunlight. Accordingly, merely wearing clothing, especially light weight summer clothing, does not necessarily provide skin beneath the clothing with adequate protection against damage from UV radiation. Although clothing which is thick and/or tightly woven may provide a reasonable level of protection to skin beneath it, such clothing is not practical in hot sunny climates from the standpoint of the personal comfort of the wearer.

There is a need, therefore, to provide protection against UV radiation for skin which is covered by clothing, especially lightweight summer clothing which is undyed. Such lightweight summer clothing normally has a density of less than 200 g/m² and has a sun protection factor (SPF) rating of between 5 and 10, depending on the type of fiber from which the clothing is manufactured.

The SPF rating of a sun protectant (sun cream or clothing) may be defined as the multiple of the time taken for the average person wearing the sun protectant to suffer sun burning under average exposure to sun. For example, if an average person would normally suffer sun burn after 30 minutes under standard exposure conditions, a sun protectant having an SPF rating of 5 would extend the period of protection from 30 minutes to 2 hours and 30 minutes. For people living in especially sunny climates, where mean sun burn times are minimal, e.g. only 15 minutes for an average fair-skinned person at mid day, SPF ratings of at least 20 are desired for lightweight clothing. In practice this means reducing the amount of UV light passing through a lightweight textile fabric by 50% or more.

In patent specification WO 94/4515, there is described, inter alia, a method of increasing the SPF rating of a fiber or fabric which comprises applying a UV absorber to a fabric having a density of less than 200 g/m², whereby the UV absorber is attached to the fiber and an application of less than 3% UV absorber based on the weight of fiber produces an SPF rating of greater than 20 for the UV absorber and fabric combination. Among the UV absorbers generically disclosed therein are those having a UV-absorbing group attached to a fiber-reactive dihalotriazine.

Surprisingly, it has now been found that the treatment of textile fibers with a UV absorber having either two UV-absorbing groups or one UV-absorbing group and one water-solubilizing group attached to a monohalotriazine significantly reduces the amount of UV light passing through fabrics produced from such treated fibers.

Accordingly, the present invention provides a method for the treatment of textile fibers comprising treating a textile fiber with 0. 1 to 6.0 %, by weight on the fiber, of a UV absorber of the formula (1)

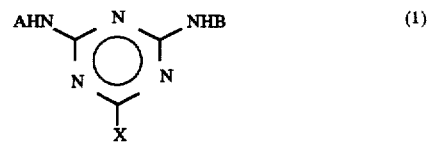

wherein A is the radical of a UV absorber, B is the radical of a UV absorber or is a water-solubilizing group and X is F or Cl, preferably Cl.

The UV absorbing groups A and B may be the same or different and are selected from suitable radicals of essentially any UV absorbing compounds; however, if both A and B are UV absorbing groups, at least one of them is advantageously substituted by at least one SO₃H, COOH or phenolic OH group or a salt thereof.

Typical radicals of UV absorbers which may be used in this invention are disclosed in U.S. Pat. No. 5,098,445 and the references cited therein, all of which are incorporated by reference.

Preferably the UV-absorbing radicals A and B are independently selected from the group consisting of radicals of the formulae:

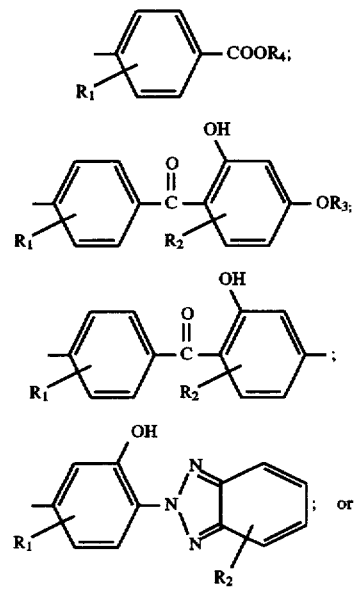

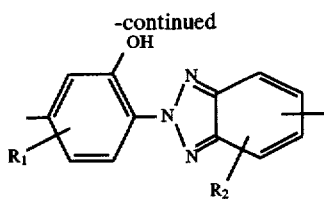

wherein $R_1$ and $R_2$ are each hydrogen, $C_1$–$C_{18}$alkyl, $C_1$–$C_{18}$alkoxy, halogen, nitro, hydroxy, COOM or $SO_3M$ in which M is hydrogen, an amine salt or an alkali metal salt, and $R_3$ and $R_4$ are each hydrogen or $C_1$–$C_{18}$alkyl.

Preferably $R_1$ and $R_2$ are each hydrogen, $C_1$–$C_7$alkyl, $C_1$–$C_7$alkoxy, hydroxy, COOM or $SO_3M$. More preferably $R_1$ and $R_2$ are each hydrogen or $C_1$–$C_4$alkyl, $C_1$–$C_4$alkoxy, hydroxy, COOM or $SO_3M$. Preferably M is a sodium ion.

Preferably $R_3$ and $R_4$ are each hydrogen or $C_1$–$C_7$alkyl, more preferably hydrogen or $C_1$–$C_4$alkyl.

It is also preferred that the water-solubilizing group be of the formula:

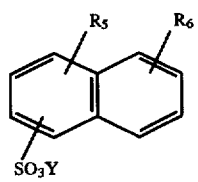

where Y is an amine salt or an alkali metal salt and $R_5$ and $R_6$ are each hydrogen, $C_1$–$C_{18}$alkyl, $C_1$–$C_{18}$alkoxy, halogen, nitro, hydroxy, COOY or $SO_3Y$. Preferably $R_5$ and $R_6$ are each hydrogen, $C_1$–$C_{18}$alkyl, $C_1$–$C_{18}$alkoxy, hydroxy or $SO_3Y$.

Other solubilizing groups will be apparent to those of ordinary skill in the dyestuff art.

The compounds of formula (1) can be prepared by reacting compounds A—$NH_2$ and B—$NH_2$ with cyanuric acid trihalide. Basically a monoamine-substituted UV absorber is reacted with a trihalo triazine. This product is then reacted with either another amino-substituted UV absorber or a solubilizing moiety. Alternatively, an amino-substituted solubilizing moiety can be reacted with the trihalo triazine first and then an amino-substituted UV absorber is reacted with the product.

The starting mines, A—$NH_2$ and B—$NH_2$, are known compounds which are readily available.

A number of compounds of the formula (1) wherein A and B are as defined above and which are suitable for use in this invention are known from U S. Pat. Nos. 4,963,160, 4,929,250 and 5,098,445, where they are disclosed as UV-absorbing agents for bonding to hydrogel contact lenses.

Compounds of the formula (1) which are particularly preferred for use in the present invention are those of the formulae

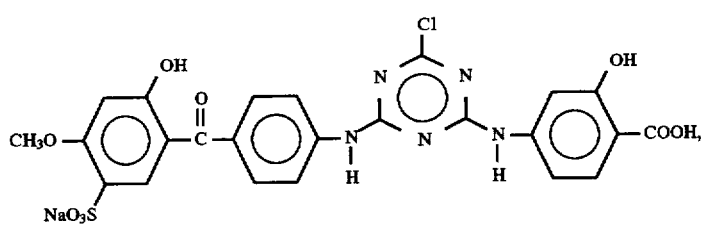

(2)

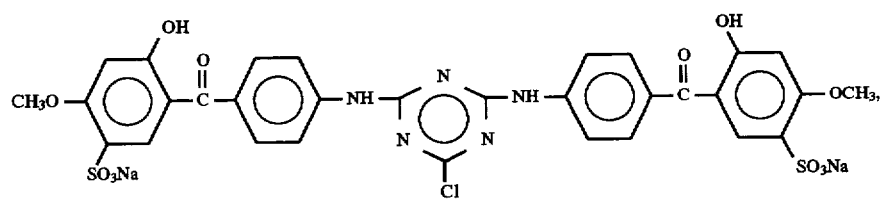

(3)

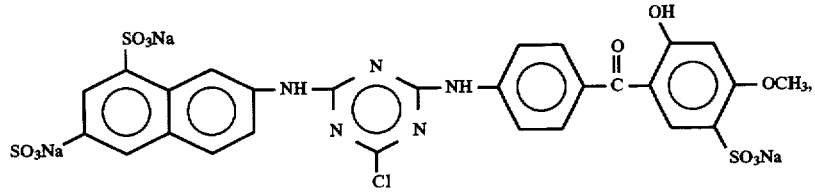

(4)

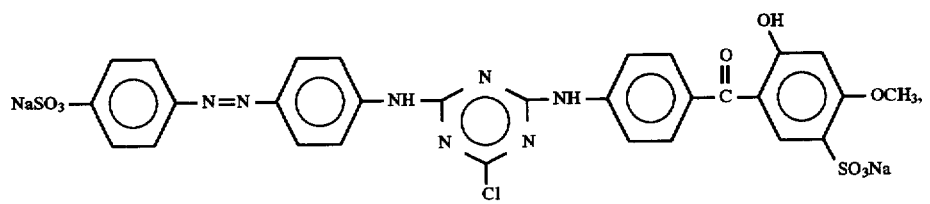

(5)

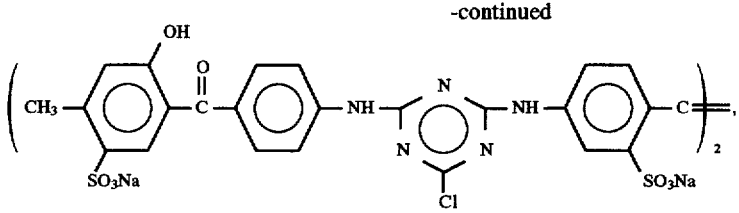

(6)

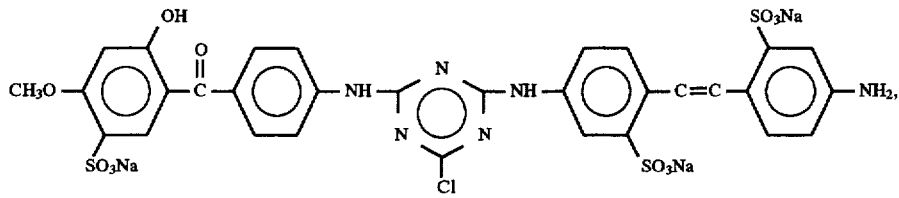

(7)

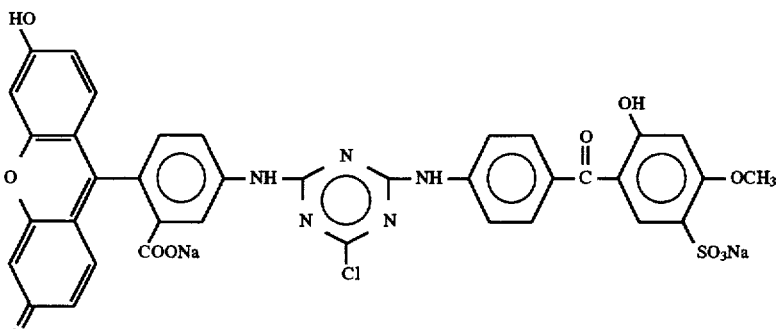

(8)

and

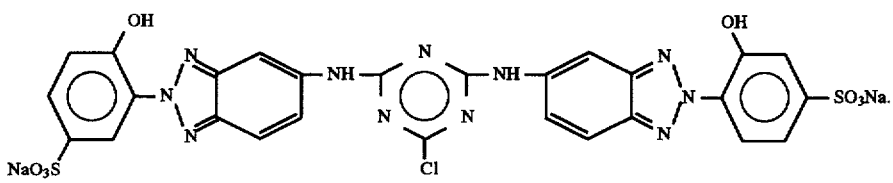

(9)

Of these, the compounds of the formulae (5), (6), (7) and (8) are believed to be novel. They and their use are another object of this invention.

The method of the present invention comprises treating a textile fiber material with 0.1 to 6.0%, preferably 0.3 to 3.0% by weight, based on the weight of the textile fiber material, of one or more compounds of the formula (1).

The textile fibers treated according to the method of the present invention may be natural or synthetic fibers or mixtures thereof. Examples of natural fibers include vegetable fibers such as cotton, viscose, flax, rayon and linen, preferably cotton, and animal fibers such as wool, mohair, cashmere, angora and silk, preferably wool. Synthetic fibers include polyester, polyamide, polyacrylonitrile and polyurethanes such as spandex fibers.

Preferably, the textile fibers treated according to the method of the present invention have a density of less than 200 g/m².

The treatment may be carried out in an analogous manner to the methods generally used to apply reactive dyes to textile materials. Depending on the compound of formula (1) used, it may be beneficial to carry out the treatment in a neutral or an alkaline bath. The method is usually conducted in an alkaline bath in the temperature range of from 20° to 140° C., for example at or near the boiling point of the aqueous bath, e.g. at about 90° C.

Solutions of the compound of formula (1), or its emulsions in organic solvents may also be used in the method of the present invention. For example, the so-called solvent dyeing (pad thermofix application) or exhaust dyeing methods in dyeing machines may be used.

If the method of the present invention is combined with a textile treatment or finishing method, the combined treatment may be advantageously carried out using appropriate stable preparations which contain a compound of formula (1) in a concentration such that the desired reduction in the amount of UV light passing through a lightweight textile fabric is achieved.

In certain cases, the compound of formula (1) is made fully effective by an after-treatment. This may comprise a chemical treatment such as treatment with an acid acceptor, a thermal treatment or a combined thermal/chemical treatment.

In addition to the compound of formula (1), a minor proportion of one or more adjuvants may also be employed in the method of the present invention. Examples of adjuvants include emulsifiers, perfumes, opacifiers, optical whitening agents, bacteriocides, nonionic surfactants, fabric care ingredients, especially fabric softeners, stain release or stain repellant ingredients or water-proofing agents, anti-gelling agents such as nitrites or nitrates of alkali metals, especially sodium nitrate, and corrosion inhibitors such as sodium silicate.

The amount of each of these optional adjuvants should not exceed 1% by weight on the treated fiber.

The method of the present invention, in addition to providing protection to the skin, also increases the useful life of a textile article treated according to the present invention. In particular, the tear resistance and/or lightfastness of the treated textile fiber material may be improved.

Accordingly, the present invention still further provides a method of reducing the amount of UV light passing through a textile fiber material, which comprises treating the textile fiber material with 0.1 to 6.0%, preferably 0.3 to 3.0% by weight, based on the weight of the textile fiber material, of one or more compounds of the formula (1).

The present invention also provides a textile fabric produced from fibers treated according to the method of the present invention as well as an article of clothing produced from the fabric.

Such textile fabrics and articles of clothing produced from the said fabrics typically have an SPF rating of 20 and above whereas lightweight untreated cotton, for example, may have an SPF rating as low as about 5. Further, since the UV absorber is chemically bonded to hydrophilic textile fibers such as cotton and nylon, repeated laundering does not significantly decrease the UV protection afforded by the treatment.

The following Examples further illustrate the present invention. However the invention is not limited thereto.

EXAMPLE 1

Preparation of the compound of the formula (5)

Cyanuric chloride, 5.1 g, is dissolved in 50 ml of warm acetone and the solution is poured into 250 ml of an ice/water mixture. To this stirred cyanuric chloride suspension at 0° C. is added 12.7 g of 4'-amino-2-hydroxy-4-methoxy-5-sulfobenzophenone, sodium salt, along with a few drops of Silwet® L-7500 surfactant (Union Carbide Corp.) and the pH is adjusted to 4.0 with 10% NaOH. The mixture is allowed to warm up to 2° to 5° C. and stirred for a total of one hour while maintaining the pH at about 4.0. Then a slurry of 17.9 g of 4-(4-aminophenylazo)benzenesulfonic acid, sodium salt, (45–50% assay, from Sandoz Chemicals) in 100 ml of water is added. The reaction mixture is heated to 45° C. and the pH is adjusted to 8.0 with 10% NaOH. The mixture is stirred for 45 minutes while maintaining the pH at about 8.0 with 10% NaOH. Then it is cooled back to room temperature and the pH is adjusted to 7.0 with 3N HCl. The total volume of the deep orange-yellow solution is 850 ml, of which 20 ml is used to prepare test solutions. The remaining solution is freeze dried to afford 30.5 g of deep yellow powder.

EXAMPLE 2

Preparation of the compound of the formula (8)

Cyanuric chloride, 5.1 g, is dissolved in 50 ml of warm acetone and the solution is poured into 250 ml of an ice/water mixture. To this stirred cyanuric chloride suspension at 0° C. is added 12.7 g of 4'-amino-2-hydroxy-4-methoxy-5-sulfobenzophenone, sodium salt, along with a few drops of Silwet® L-7500 surfactant (Union Carbide Corp.) and the pH is adjusted to 4.0 with 10% NaOH. The mixture is allowed to warm up to 2° to 5° C. and stirred for a total of one hour while maintaining the pH at about 4.0. Then 3.7 g of fluoresceinamine, isomer I (Aldrich Chemical Co., Inc.) is added. The reaction mixture is heated to 45° C. and the pH is adjusted to 8.5. The mixture is stirred for 45 minutes while maintaining the pH at about 8.5. Then it is cooled back to room temperature and the pH is adjusted to 7.0 with 3N HCl. The solution is freeze dried to afford 19.9 g of orange-colored solid.

EXAMPLE 3

Preparation of the compound of the formula (7)

The compound of the formula (7) is prepared analogously to the compound of the formula (8), but replacing the fluoresceinamine by 15.5 g of 4,4'-diaminostilbene-2,2'-disulfonic acid. Freeze drying the solution affords 31.46 g of yellow solid.

EXAMPLE 4

Preparation of the compound of the formula (6).

The compound of the formula (6) is prepared analogously to the compound of the formula (8), but replacing the fluoresceinamine by 7.8 g of 4,4'-diaminostilbene-2,2'-disulfonic acid. Freeze drying the solution affords 25.1 g of light yellow solid.

EXAMPLE 5

The following exhaust dyeing procedure is used to apply 3% by weight of various compounds of the formula (1) to lightweight, undyed 100% cotton swatches having a density of 119 g/m$^2$.

1) Prewet fabric with 0.5 g/l Silvatol® SO in hot water (140° F.; 60° C.) and rinse well.
2) Add 150 g water to application bath (use 15:1 dye:liquor ratio, i.e. 15 g water per g of fabric).
3) Heat the bath to 175° F. (80° C).
   Silvatol is a registered trademark of Ciba-Geigy.

Cycle 1—45 min

4) Add: 1 g of reserve salt (i.e. 1% on weight of fabric) to bath.
5) Add x g UV Absorber solution (prepared by dissolving 1 g UV Absorber in 99 g water).
6) Add 12 g NaCl (=80 g/l salt) to bath.
7) Add 10 g cotton fabric.
8) Circulate 15 minutes.
9) Add 1.5 g Na$_2$CO$_3$ (=10 g/l soda ash).
10) Circulate 15 min.
11) Slowly add 0.375 g 50% NaOH.
12) Circulate 15 min.

Cycle 2—Exhaustion

13) Circulate for another 45 min. after the end of the 1st cycle.
14) Rinse fabric with 100 ml hot water for 10 min. (10:1 ratio, each piece rinsed separately).

Cycle 3—Soaping and Final Rinse

15) Set bath (200 ml) at 200° F. (87° C.).
16) Add 0.05 g Silvatol AS and fabric; soap for 10 min.
17) Rinse fabric with 200 ml hot water followed by 200 ml cold water.
18) Dry fabric at room temperature.

A modified UV spectrometer is used to measure the mount of UV light between the wavelengths of 300 to 400 nanometers transmitted through lightweight, undyed 100% cotton swatches having a density of 119 g/m$^2$ and treated according to the above procedure with 3% by weight of various compounds of the formula (1) versus control swatches of the same fabric which were subjected to the same procedure but without the UV absorber of the formula (1). The following compounds of the formula (1) were employed:

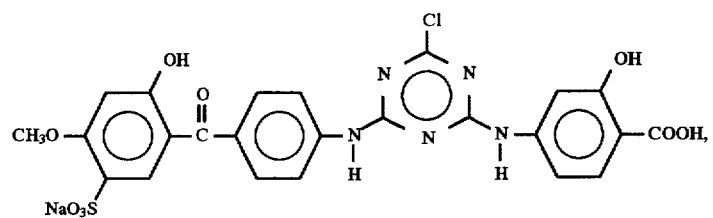
(2)
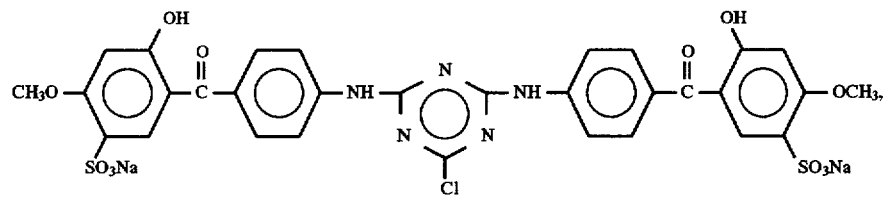
(3)
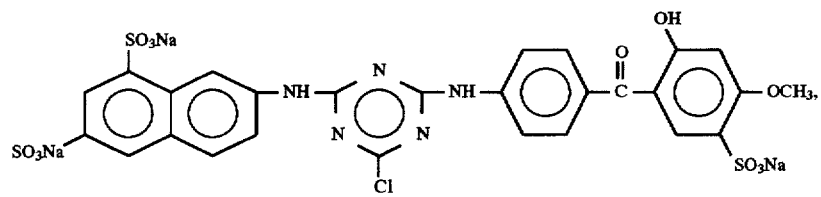
(4)
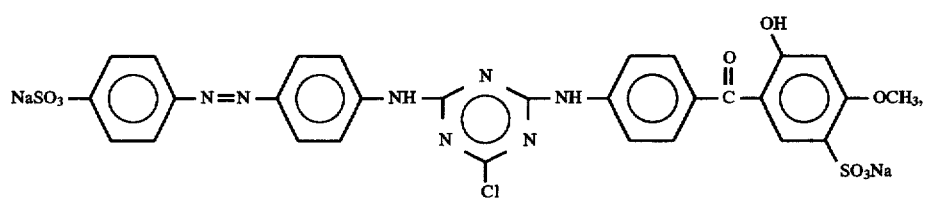
(5)
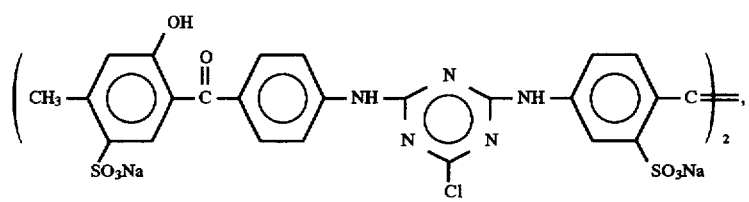
(6)
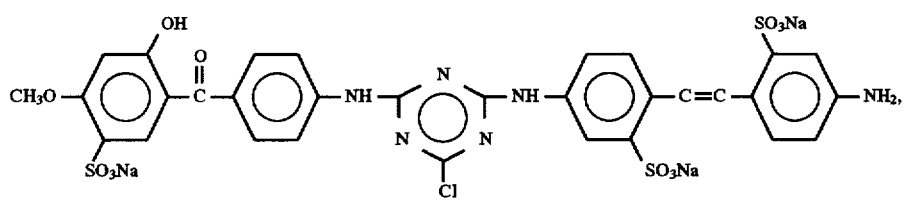
(7)
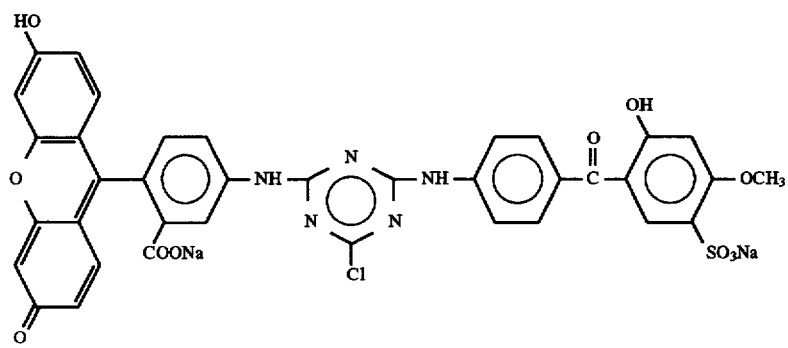
(8)
and

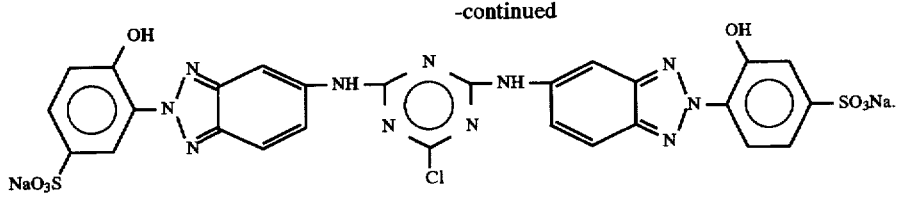

The results are shown in the following table.

| Compound No. | UV Transmission, % |
| --- | --- |
| (2) | 50 |
| (3) | 50 |
| (4) | 50 |
| (5) | 24 |
| (6) | 22 |
| (7) | 24 |
| (8) | 37 |
| (9) | 30. |

The lower the % transmission, the more effective the compound of formula (1) is in preventing UV light from passing through the fabric.

EXAMPLE 6

Lightweight, undyed 100% cotton swatches having a density of 119 g/m² and treated according to the procedure of Example 5 with 3% by weight of the compound of the formula (2) were subjected to repeated launderings according to AATCC Test Method 61-1986. Then the amount of UV light between the wavelengths of 300 to 400 nanometers transmitted through the laundered samples was measured versus untreated laundered controls according to the procedure of Example 1. The results are shown in the following table.

| No. of Washes | UV Transmission, % |
| --- | --- |
| 1 | 52 |
| 2 | 45 |
| 3 | 45 |
| 4 | 45.5 |

The results of this very vigorous test demonstrate that the effectiveness of the inventive fabric treatment is not significantly affected by repeated laundering, i.e. it is permanent.

What is claimed is:

1. A method of improving the tear resistance of a textile fiber material, which comprises treating the textile fiber material with 0.1 to 6.0% based on the weight of the textile fiber material, of a compound of the formula (1)

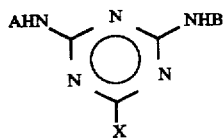

wherein A is the radical of a UV absorber, B is the radical of a UV absorber and X is F or Cl,
with the proviso that at least one of A and B is substituted by at least one SO₃H or COOH group or a salt thereof which is bonded directly to an aromatic ring.

2. A method of reducing the amount of UV light passing through a textile fiber material, which comprises treating the textile fiber material with 0.1 to 6.0% based on the weight of the textile fiber material, of a compound of the formula (1)

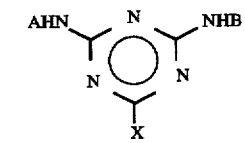

wherein A is the radical of a UV absorber, B is the radical of a UV absorber and X is F or Cl, with the proviso that at least one of A and B is substituted by at least one SO₃H or COOH group or a salt thereof which is bonded directly to an aromatic ring.

3. A method according to claim 2, wherein X is Cl.

4. A method according to claim 2, wherein the UV-absorbing radicals A and B are independently selected from the group consisting of radicals of the formulae:

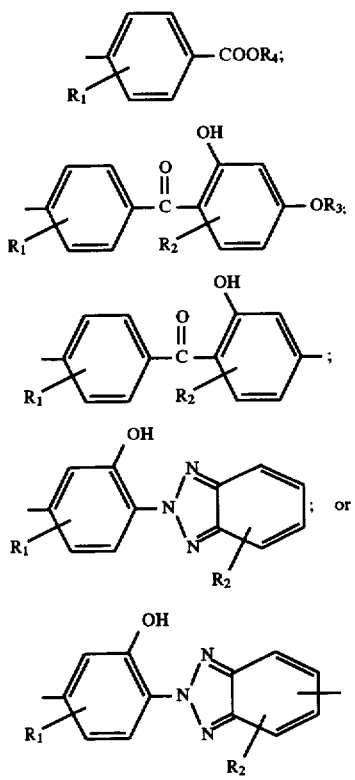

wherein $R_1$ and $R_2$ are independently hydrogen, $C_1$–$C_{18}$alkyl, $C_1$–$C_{18}$alkoxy, halogen, nitro, hydroxy, COOM or SO₃M in which M is hydrogen, an amine the cation of or an alkali metal and $R_3$ and $R_4$ are each hydrogen or $C_1$–$C_{18}$alkyl.

5. A method according to claim 4, wherein $R_1$ and $R_2$ are independently hydrogen, $C_1$–$C_7$alkyl, $C_1$–$C_7$alkoxy, hydroxy, COOM or SO₃M.

6. A method according to claim 5, wherein $R_1$ and $R_2$ are independently hydrogen or $C_1$-$C_4$alkyl, $C_1$-$C_4$alkoxy, hydroxy, COOM or $SO_3M$.

7. A method according to claim 4, wherein M is a sodium cation.

8. A method according to claim 4, wherein $R_3$ and $R_4$ are each hydrogen or $C_1$-$C_7$alkyl.

9. A method according to claim 2, wherein the compound of the formula (1) is selected from the group consisting of

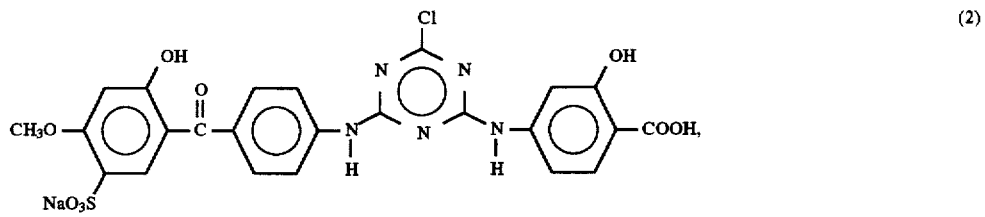

(2)

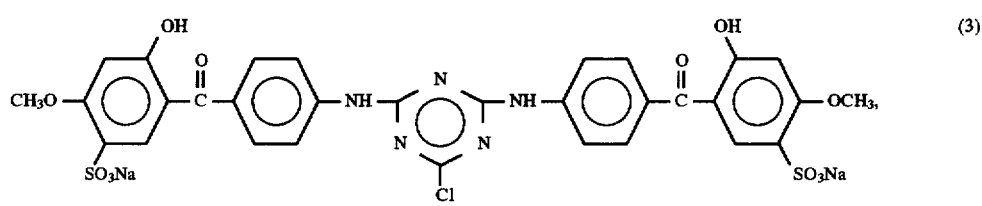

(3)

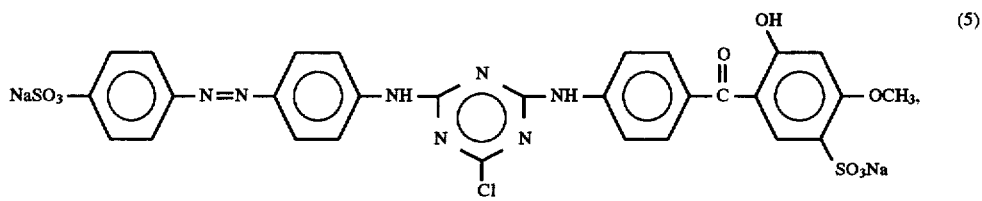

(5)

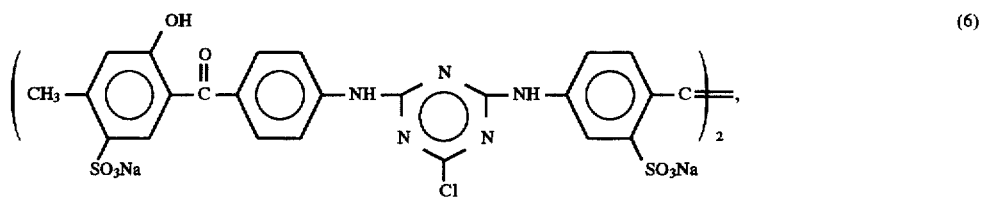

(6)

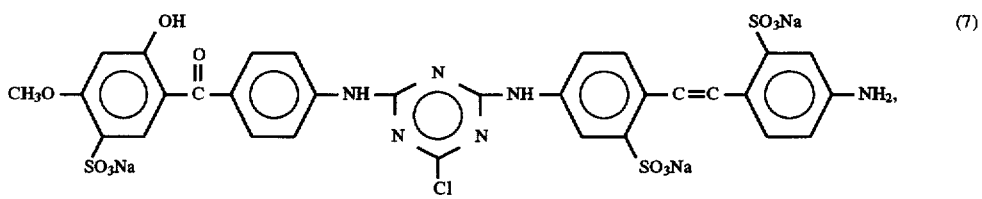

(7)

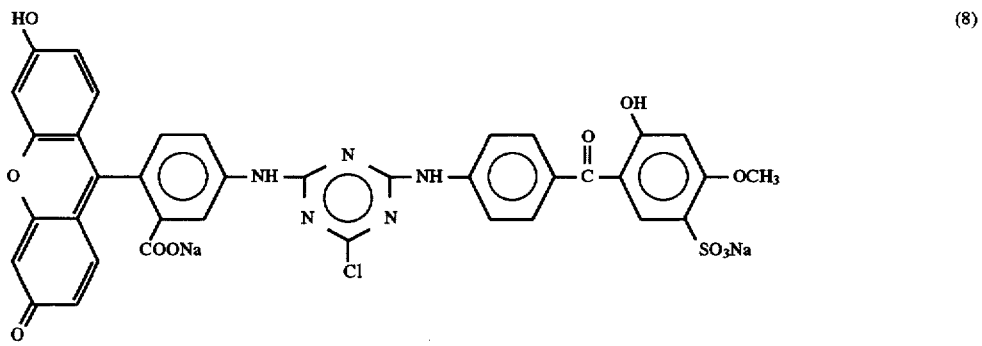

(8)

and

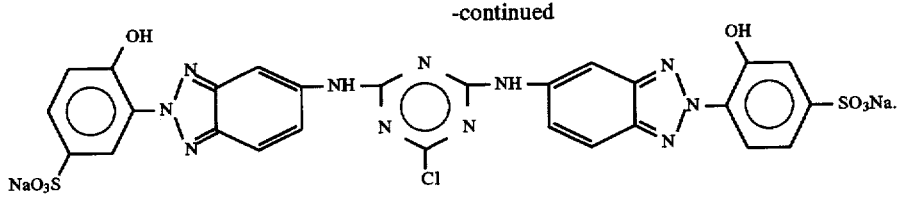 (9)

10. A method according to claim 2, which comprises treating a textile fiber with 0.3 to 3.0%, by weight on the fiber, of a UV absorber of the formula (1).

11. A method according to claim 2, wherein the textile fiber is a natural or synthetic fiber or a mixture thereof.

12. A method according to claim 11, wherein the textile fiber is cotton, viscose, flax, rayon, linen, cotton, wool, mohair, cashmere, angora or silk.

13. A method according to claim 12, wherein the textile fiber is cotton.

14. A method according to claim 11, wherein the textile fiber is polyester, polyamide, polyacrylonitrile or polyurethane.

15. A textile fabric produced from fibers treated according to the method of claim 1.

16. An article of clothing produced from the textile fabric according to claim 15.

* * * * *